US010568575B2

(12) United States Patent
Martin et al.

(10) Patent No.: US 10,568,575 B2
(45) Date of Patent: Feb. 25, 2020

(54) DIAGNOSTIC MEASUREMENT APPARATUS

(71) Applicant: Becton, Dickinson and Company, Franklin Lakes, NJ (US)

(72) Inventors: Adam Martin, Holly Springs, NC (US); Mircea Stefan Despa, Cary, NC (US); Dylan Wilson, Chapel Hill, NC (US); Sundeep Kankanala, Le Pont-de-Claix (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 114 days.

(21) Appl. No.: 15/598,171

(22) Filed: May 17, 2017

(65) Prior Publication Data

US 2017/0332969 A1 Nov. 23, 2017

Related U.S. Application Data

(60) Provisional application No. 62/338,932, filed on May 19, 2016.

(51) Int. Cl.
*A61B 5/22* (2006.01)
*A61B 5/00* (2006.01)
*A61B 5/11* (2006.01)
*G16H 40/63* (2018.01)
*G16H 20/17* (2018.01)
(Continued)

(52) U.S. Cl.
CPC .......... *A61B 5/6848* (2013.01); *A61B 5/0004* (2013.01); *A61B 5/03* (2013.01); *A61B 5/1114* (2013.01); *A61B 5/22* (2013.01); *A61B 5/225* (2013.01); *A61M 5/20* (2013.01); *G16H 20/17* (2018.01); *G16H 40/63* (2018.01); *A61B 5/1121* (2013.01); *A61B 5/4842* (2013.01); *A61M 2205/332* (2013.01); *A61M 2205/3576* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/583* (2013.01)

(58) Field of Classification Search
CPC ........... A61B 5/6848; A61B 5/22; A61M 5/20
See application file for complete search history.

(56) References Cited

U.S. PATENT DOCUMENTS 9,317,916 B1 4/2016 Hanina et al.
2011/0034784 A1* 2/2011 David .................. A61B 5/0205
600/301

(Continued)

FOREIGN PATENT DOCUMENTS

WO WO 2016/026679 A1 2/2016

OTHER PUBLICATIONS

International Search Report and Written Opinion of the International Searching Authority dated Aug. 24, 2017, for International Application No. PCT/US2017/033141 filed May 17, 2017.

*Primary Examiner* — Puya Agahi
(74) *Attorney, Agent, or Firm* — Knobbe Martens Olson & Bear, LLP

(57) ABSTRACT

A system for detecting disease progression can include an injection device configured to deliver medicament to a patient, one or more load sensors, one or more motion sensors, and a processor configured to read data from one or more of the load sensors and motion sensors and produce an output for display to a user.

20 Claims, 6 Drawing Sheets

(51) Int. Cl.
*A61B 5/03* (2006.01)
*A61M 5/20* (2006.01)

(56) References Cited

U.S. PATENT DOCUMENTS

| | | | |
|---|---|---|---|
| 2012/0330571 A1 | 12/2012 | LaCourse et al. | |
| 2016/0220863 A1* | 8/2016 | Braier | A63B 23/16 |
| 2017/0164832 A1* | 6/2017 | Kaib | A61N 1/3968 |
| 2017/0224573 A1* | 8/2017 | Challa | A45B 9/04 |
| 2017/0291066 A1* | 10/2017 | Le Chevalier | A61B 5/1079 |

\* cited by examiner

DIAGNOSTIC MEASUREMENT APPARATUS

RELATED U.S. APPLICATIONS

This application claims priority to U.S. Provisional Appl. No. 62/338,932 filed on May 19, 2016, which is hereby incorporated by reference in its entirety.

BACKGROUND OF THE INVENTION

Field of the Invention

This invention relates to injection devices, and more particularly, relates to mechanical and electromechanical autoinjectors for injecting liquid medicine into patients in need of therapeutic treatments.

Description of the Related Art

Autoinjectors are medical devices that allow patients to self-administer their medications outside a hospital or physician's office. These devices are often used for the management of chronic diseases, such as diabetes, rheumatoid arthritis, multiple sclerosis, and osteoporosis. A typical autoinjector consists of a prefilled syringe in a mechanical device that deploys a needle and delivers a medicament with a single push of a release button. While autoinjectors allow for convenient self-administration, these devices do not provide feedback to the user, or the user's physician, regarding the state or progression of the disease. Accordingly, prior to using an autoinjector to administer medicine, or during the use of an autoinjector, a patient may need to visit a physician or physical therapist to be given certain diagnostic tests which can be indicative of the patient's health or the efficacy of the treatment. Based on the results of these tests, the physician may change the course of treatment for the patient.

SUMMARY OF THE INVENTION

Aspects of the invention include systems, devices, and methods for diagnostic measurement using an injection device.

One embodiment is a system for performing diagnostic measurement of a disease. The system includes an injection device configured to deliver medicament to a patient and also including one or more diagnostic sensors. One example of a diagnostic sensor is a force sensor. The system may also include one or more motion sensors, and a processor configured to read data from one or more of the force sensors and motion sensors. In one embodiment, the processor may be configured to display a measurement based on data from one or more of the force sensors or motion sensors.

Another embodiment is a method of performing diagnostic testing of a patient. The method includes providing an injection device configured to administer a medicament and measure a diagnostic parameter from the patient. The method can include reading the diagnostic parameter from a sensor attached to the injection device and produce a measurement relevant to health or disease progression based at least in part on the detected data.

DETAILED DESCRIPTION

Figure 1:
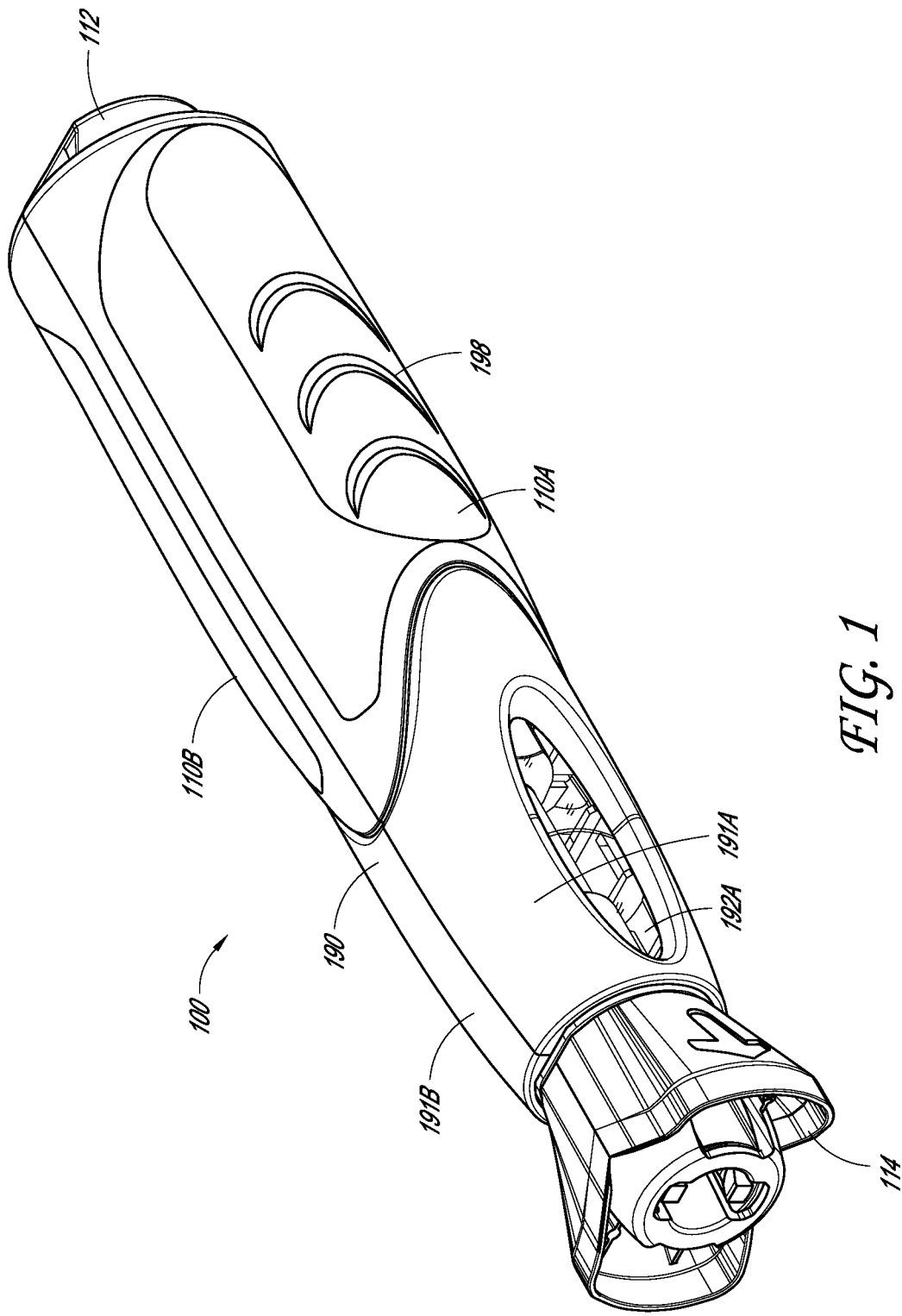
FIG. 1 depicts a perspective view of a diagnostic measurement device configured for diagnostic measurement in accordance with an illustrative embodiment of the present invention.

As will be appreciated by one skilled in the art, there are numerous ways of carrying out the examples, improvements, and arrangements of a medicament delivery device in accordance with embodiments of the invention disclosed herein. Although reference will be made to the illustrative embodiments depicted in the drawings and the following description, these embodiments are not meant to be exhaustive of the various alternative designs and embodiments that are encompassed by the disclosed invention. Those skilled in the art will readily appreciate that various modifications may be made, and various combinations can be made, without departing from the invention.

Embodiments of a diagnostic measurement device are depicted in FIGS. 1-5. One embodiment of a diagnostic measurement device includes one or more force sensors designed to fit within the interior space of an injection device, such as an autoinjector. For example, the force sensors may be adapted to fit within an interior space of a PHYSIOJECT™ autoinjector from Becton Dickinson®. In this embodiment, the force sensors are configured to fit beneath an exterior surface of the injection device. The force sensors may also be adapted to couple with the exterior surface of an injection device. In some embodiments, the force sensors may be housed within the interior of a separate module which can fit within the interior of the injection device or attach to the exterior of the injection device. The force sensors can be configured to detect an external force, or load, applied to an exterior section of the injection device. In one embodiment, the force sensors are configured to measure the compressive force of a patient's hand and fingers as the patient squeezes the injection device. A patient using the diagnostic measurement device can be instructed to grip and squeeze the force sensors so that their grip strength can be measured. This data can be displayed or transmitted to a health care provider so that the grip strength of the patient can be monitored over time. Patients suffering from diseases that can affect their strength can thereby be conveniently monitored using the same device they have for taking their medicine.

The injection device may further include one or more motion sensors, such as a gyroscope or accelerometer, configured to detect movement and/or orientation of the diagnostic measurement device. The motion sensors may be positioned within the interior of the injection device. Alternatively, the motion sensors may be positioned on the exterior of the injection device or within the interior of a separate module, which can fit within the interior or attach to the exterior of the injection device. The motion sensors can be programmed to detect the range of motion or other parameters of the patient. The diagnostic device may be programmed to display a specific set of movements for the user to undertake. For example, the diagnostic device may be programmed to ask the patient to raise and lower his or her arms. The diagnostic device may also be programmed to ask the patient to swing their arms in a circular motion or to otherwise move or rotate their arms or wrists in a particular motion. As the patient makes these movements, the device can measure its position in three-dimensional space and thereby determine if the patient's range of motion of their arms and/or wrists has changed over time.

In an illustrative embodiment the diagnostic measurement device may further include a processor configured to process data from the force sensors and/or motion sensors to produce measurements related to force, orientation, and movement. In some embodiments, the processor can be programmed to produce a grip strength measurement for describing a patient's grip strength based on data detected by the force sensors. The processor can further be programmed to produce a range of motion measurement for describing the range of motion of a patient's hand or arms based on data received from the motion sensors.

The diagnostic measurement device may further include a display for displaying force and motion measurements and/or a communication module providing connectivity between the diagnostic measurement device and external devices, allowing information from the communication module to be transmitted to and received from interested parties including the patient, payers, pharmacies and clinicians. For example, the processor may be connected to an application running on a portable electronic device, such as a smart phone or tablet, or an in-home hub. This connection may be made using well-known wireless communication protocols, such as Bluetooth, WIFI, or other means. Once the application detects a connection to the diagnostic measurement device, data from the force and motion sensors may be transmitted to the application for display to the user. For example, numerical measurements corresponding to a patient's grip strength may be displayed based on data detected by the force sensors. The diagnostic device may also use the included motion sensors to determine and display a numerical rating corresponding to a user's range of motion. In other embodiments, a chart or graph showing one or more measurements may be displayed to the user. For example, a graph illustrating daily grip strength or range of motion measurements over a period of time may be displayed to the user. In some embodiments, the display or application may further be configured to provide instructions to the user for performing one or more actions relating to the proper taking of measurements by the force and/or location sensors. For example, instructions may be provided to move or rotate the grip diagnostic measurement device in one or more directions. The extent of these movements may be detected by the motion sensors and used in determining a range of motion of the user.

In one embodiment, force sensors and/or location sensors are present within an autoinjector that is configured to administer a single dose of a drug to a patient. Representative examples of drugs that may be used in such an autoinjector include ORENCIA® and HUMIRA®. Before or after administration of a dose of medicine, a user may initiate a process to measure their grip strength and/or range of motion using an application on an external device or a user interface on the autoinjector. This provides a simple and efficient mechanism that allows a patient to track their own grip strength and range of motion over time. This tracking function may be beneficial for patients having degenerative diseases, particularly when the data can be automatically transmitted from the device to a healthcare worker.

In an illustrative embodiment, the injection device may be disposable, but connected to an internal or external measurement device. In some embodiments of the present invention, a module including force and/or motion sensors may be disposable as well. In other embodiments, the module may be removed and placed in a different disposable injection device to convert it into a diagnostic measurement device.

Although various persons, including, but not limited to, a patient or a healthcare professional, can operate or use illustrative embodiments of the present invention, for brevity an operator, patient or user will be referred to as a "user" hereinafter.

Although various fluids can be employed in illustrative embodiments of the present invention, fluid in an injection device will be referred to as "medicament" hereinafter.

Although various inputs, including, but not limited to, mechanical buttons, tactile inputs, voice-controlled input, or any other inputs known in the art, can be implemented using illustrative embodiments of the present invention, for brevity an input will interchangeably be referred to as a "button" or a "trigger" hereinafter.

FIG. 1 depicts an illustrative embodiment of a diagnostic measurement device 100 configured for diagnostic measurement. At a proximal end of the diagnostic measurement device 100 is an activation button 112 configured to activate the device to release a syringe into a user when engaged. At a distal end of the diagnostic measurement device 100 is a safety cap 114 configured to prevent the user from inadvertent contact with the syringe (not shown).

The diagnostic measurement device 100 further includes a cover 190 forming the exterior of the diagnostic measurement device 100. The cover 190 includes cover pieces 191A and 191B which each form a lateral half shell that together form the outer portion of the diagnostic measurement device 100. The distal portion of the cover piece 191A includes a transparent viewing window 192A which may allow a user to view internal components of the diagnostic measurement device 100, such as the syringe. The cover 190 also includes a pair of overmolds 110A and 110B configured for placement over a plurality of force sensors (not shown) that are internal to the device 100. In some embodiments, one or more force sensors are positioned below each overmold 110A,B. The overmolds 110A,B can include textured surfaces 198 configured to provide ergonomic comfort and to provide an indication of where a user should grip the diagnostic measurement device 100. The textured surfaces 198 can also provide friction to prevent slipping of the diagnostic measurement device 100 within a hand of a user. The cover 190 may provide a protective exterior for the diagnostic measurement device 100.

Figure 2:
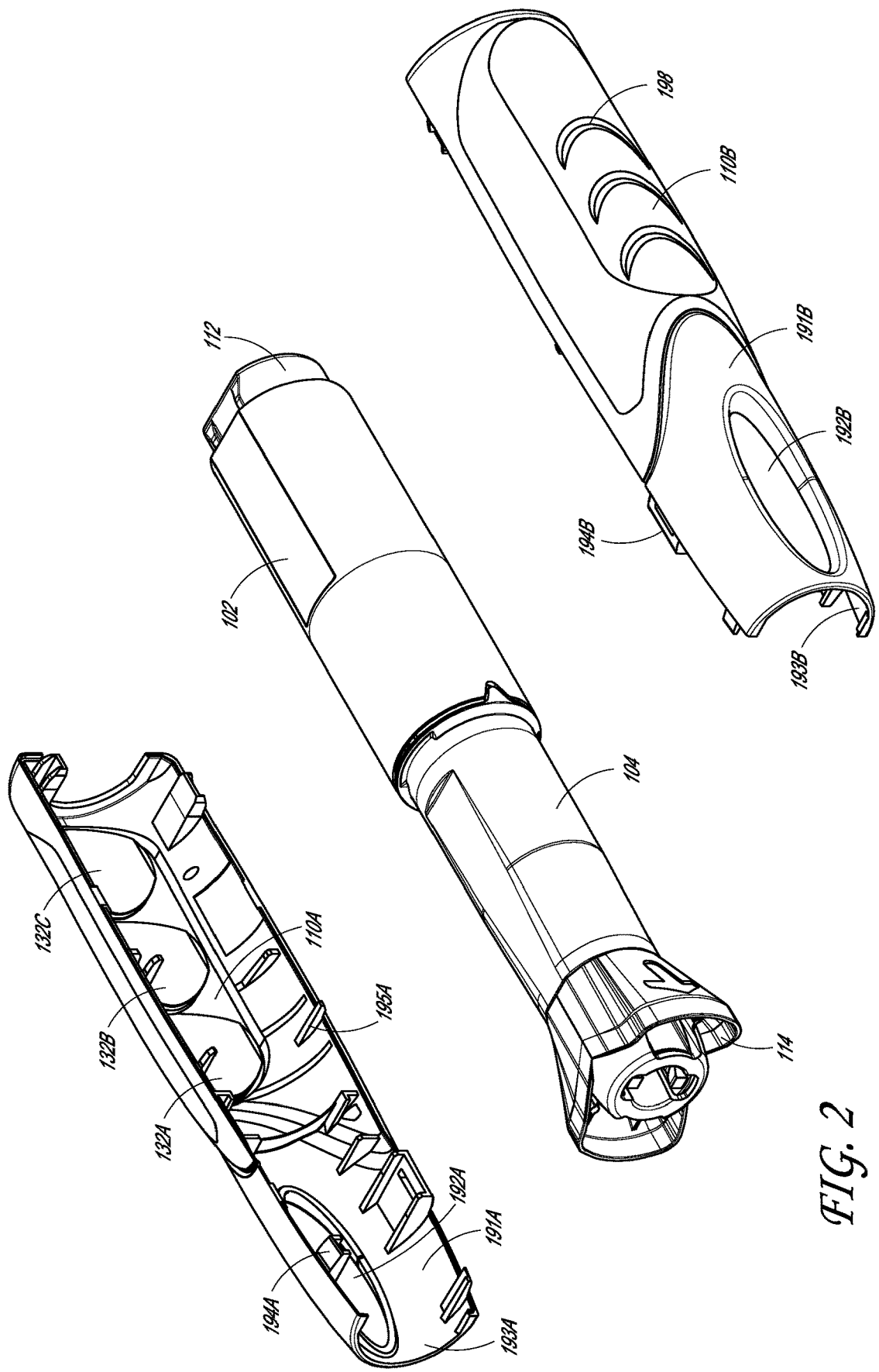
FIG. 2 depicts a partial exploded view of a diagnostic measurement device configured for diagnostic measurement in accordance with an illustrative embodiment of the present invention.

FIG. 2 depicts a partial exploded view of an illustrative embodiment of the diagnostic measurement device 100 showing cover pieces 191A and 191B separated from the remainder of the diagnostic measurement device 100. The diagnostic measurement device 100 includes an upper portion 102, which includes the activation button 112, and a transparent lower portion 104. The safety cap 114 is secured to the distal end of the lower portion 104. On the interior of the cover pieces 191A and 191B are force sensor placement features 132A-C. Each force sensor placement feature is configured to engage one of the force sensors (not shown)

attached to the side of the upper portion 102. An interior surface 193A of cover piece 191A further includes a plurality of complementary connectors 194A in order to secure to a plurality of complementary connectors 194B of the interior surface 193B of cover piece 191B. The interior surface 193A of cover piece 191A further includes a plurality of ridged portions 195A in order to engage the exterior surface of the upper portion 102 and lower portion 104. The cover piece 191B further includes a transparent viewing window 192B which may allow a user to view internal components of the diagnostic measurement device 100, such as the syringe.

Figure 3A:
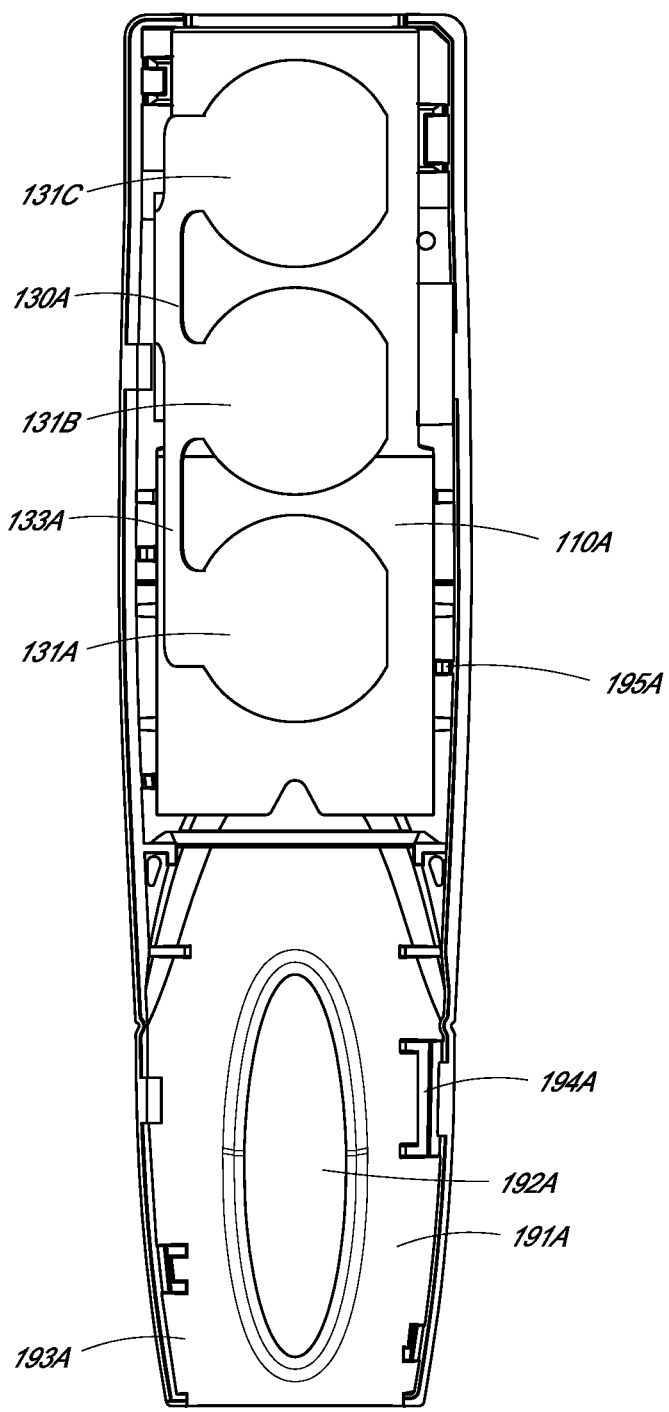
FIG. 3A depicts an interior view of the left side of a diagnostic measurement device configured for diagnostic measurement in accordance with an illustrative embodiment of the present invention.

FIG. 3A shows an interior view of the left side cover piece 191A of the diagnostic measurement device 100 showing overmold 110A of cover piece 191A engaged with a force sensor 130A. Sensor 130A includes a plurality of round sensing areas 131A-C connected by a connection piece 133A. The sensing areas 131A-C are aligned with and engage the sensor placement features 132A-C respectively. The round sensing areas 131A-C and/or sensor placement features 132A-C may include an adhesive for securing the sensor 130*a* to the sensor placement features 132A-C.

Figure 3B:
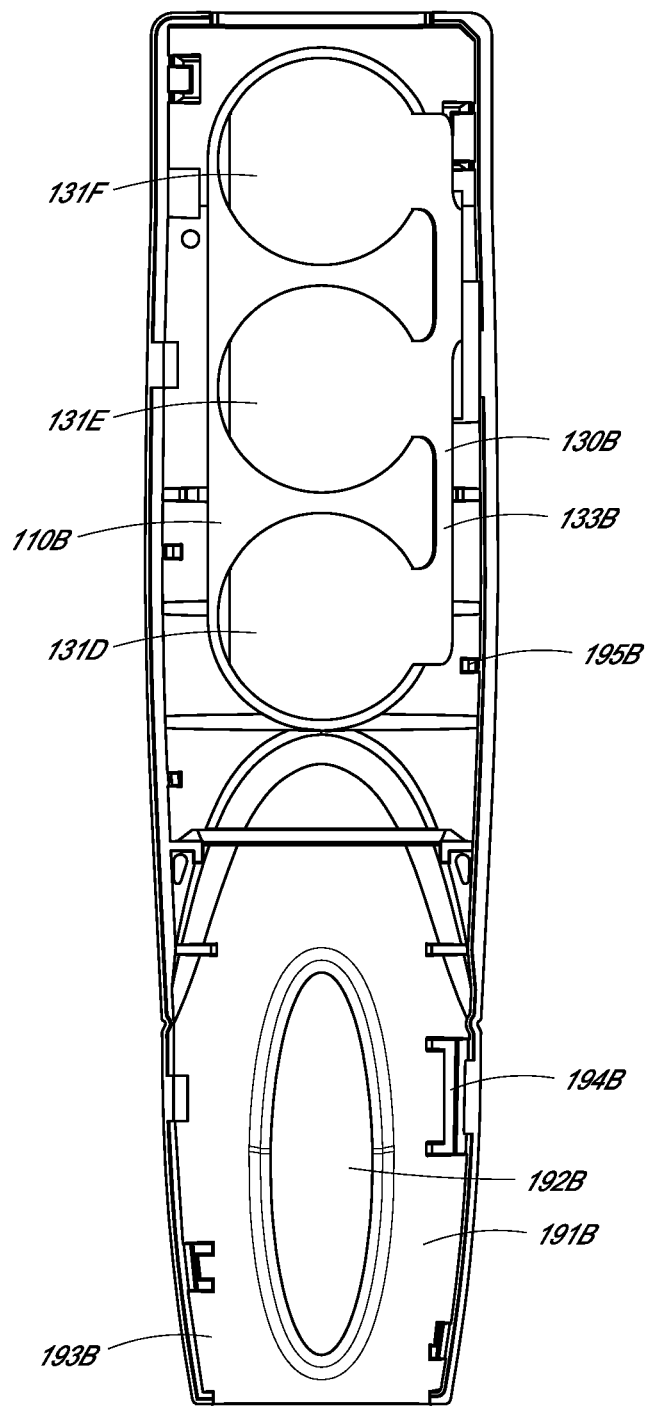
FIG. 3B depicts an interior view of the right side of a diagnostic measurement device configured for diagnostic measurement in accordance with an illustrative embodiment of the present invention.

FIG. 3B shows an interior view of the right side cover piece 191Bof the diagnostic measurement device 100 showing overmold 110B of cover piece 191B engaged with a force sensor 130B. The force sensor 130B can include a plurality of round sensing areas 131D-F connected by a connection piece 133B. The sensing areas 131D-F can align with and engage sensor placement features (not shown) on the interior side of the overmold 110B of cover piece 191B. FIG. 3B also shows a plurality of ridged portions 195B of the interior surface 193B configured to engage the exterior surface of the upper portion 102 and lower portion 104.

The sensors are configured to detect force exerted on the exterior of the overmolds 110A and 110B respectively. For example, the sensors may detect a force resulting from the squeezing of the device 100 in a hand of a user. Each force sensing area can be configured to detect the force exerted on an exterior of a section of the overmold that correlates to the location of a corresponding sensor placement feature on the interior of each the overmold. Thus, each sensing area can detect a force exerted on a different area of the diagnostic measurement device 100.

In an illustrative embodiment, each force sensor discussed above can include one or more force sensitive resistors. In some embodiments, each force sensing area includes a force sensitive resistor. Each force sensitive resistor can vary its resistance based on the amount of pressure being applied to the force sensing area. Resistance may decrease in response to an increase in applied force. The resistance can then be determined and correlated to an amount of applied force. Other resistive based sensors are also contemplated.

In alternative embodiments, the sensors may include any sensors capable of detecting force, pressure, or load, such as for example, capacitive based sensors, magnetic based sensors, optical sensors, and piezoelectric sensors.

Figure 4:
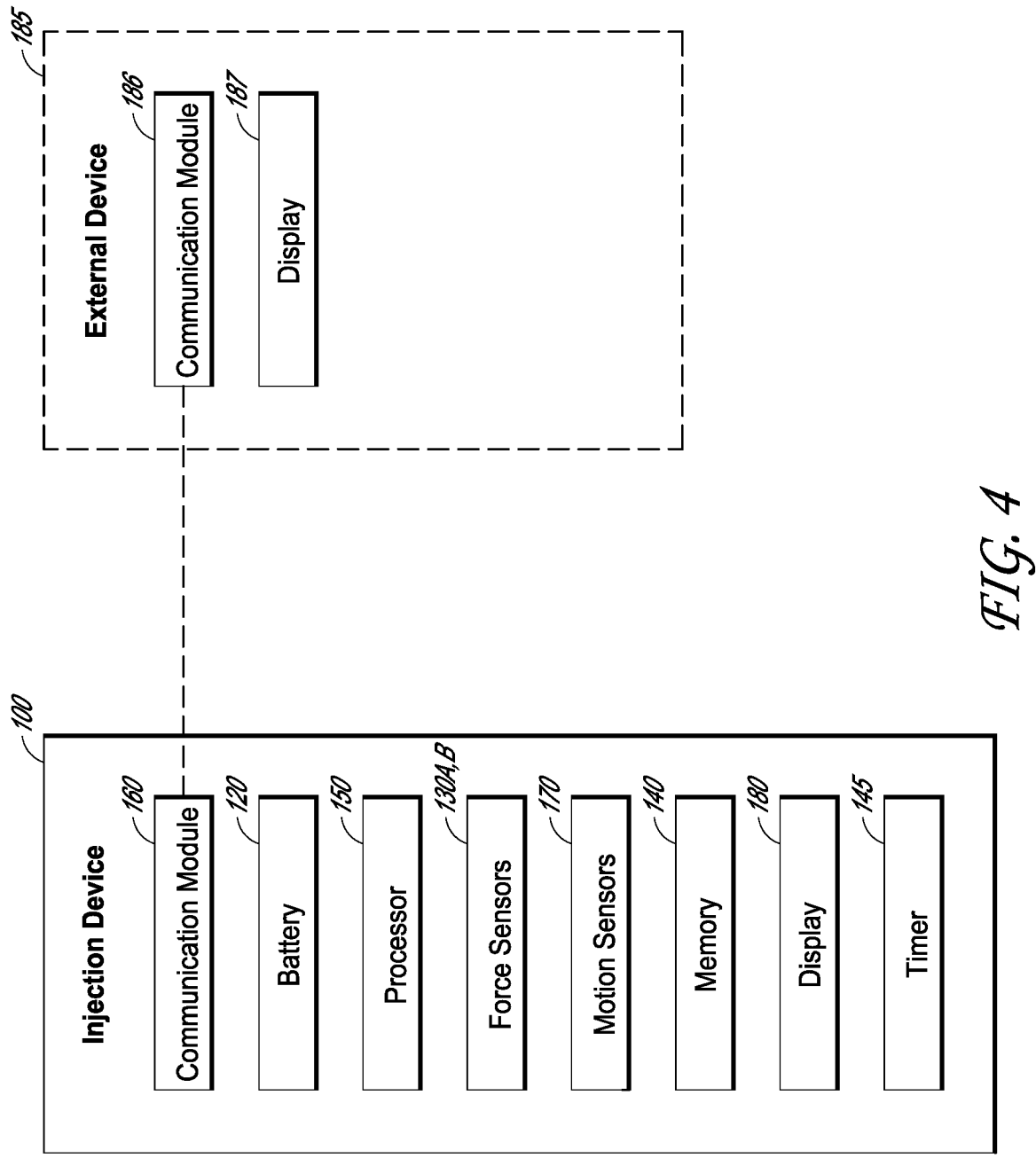
FIG. 4 depicts a schematic view of a diagnostic measurement device configured for diagnostic measurement in communication with an external device in accordance with an illustrative embodiment of the present invention.

FIG. 4 depicts a schematic view of an illustrative embodiment of the diagnostic measurement device 100 which includes a battery 120, force sensors 130A,B, one or more motion sensors 170, a processor 150, a communication module 160, a memory 140, a display 180, and a timer 145.

In an illustrative embodiment according to the present invention, the battery 120 is a CR1025 coin cell battery. In one embodiment, the battery 120 can be connected to the device 100 through an external switch. The battery 120 supplies power to the electrical components of the diagnostic measurement device 100.

The motion sensors 170 can comprise any sensors configured to detect movement and/or orientation of the diagnostic measurement device 100. For example, the motion sensors 170 can include one or more accelerometers or gyroscopes. The motion sensors 170 can include a single-axis accelerometer or a multiple-axis accelerometer.

The force sensors 130A,B and motion sensors 170 are in communication with the processor 150. The processor 150 is further in communication with the communication module 160, the memory 140, the display 180, and the timer 145.

In accordance with an illustrative embodiment, the force sensors 130A,B can be configured to detect one or more forces exerted on the exterior of the diagnostic measurement device 100. Force data from the force sensors 130A,B can be transmitted to the processor 150. The processor 150 can be programmed to process data from the force sensors 130A,B to determine one or more force measurements. Force measurements may include, but are not limited to, hand grip strength measurements. The processor 150 can also be programmed to initiate the transmission of the force measurements and/or force data to an external device, such as external device 185, via the communication module 160.

In accordance with an illustrative embodiment, the motion sensors 170 can be configured to detect one or more movements and/or orientations of the diagnostic measurement device 100. Motion data, including movement and/or orientation data, from the motion sensors 130A,B can be transmitted to the processor 150. The processor 150 can be programmed to process data from the motion sensors 170 to determine one or more motion measurements, for example movement and/or orientation measurements. Motion measurements can include, but are not limited to, wrist flexion measurements, wrist extension measurements, wrist supination measurements, wrist pronation measurements, ulnar deviation measurements, radial deviation measurements, arm rotation measurements, arm flexion measurements, arm extension measurement, arm abduction measurements, arm adduction measurements, and circumduction measurements. The processor 150 can also be programmed to initiate the transmission of the motion measurements and/or motion data to an external device, such as external device 185, via the communication module 160.

In an illustrative embodiment according to the present invention, the communication module 160 can be connected to a network by wired or wireless communication, cell communication, Bluetooth®, ZigBee®, LAN, WLAN, RF, IR, or any other communication method or system known in the art. The communication module 160 can communicate with an external device 185 such as a mobile device, home health monitor, computer, server, or any other electronic external device that is known in the art. This allows device data to be transmitted to or received from users, payers, pharmacists, physicians, nurses, family members or any other desired parties. In one embodiment, the external device includes a communication module 186 for receiving data from and transmitting data to the communication module 160. In one embodiment, the external device includes a display 187 to allow a user to read data on the external device. In one embodiment, the external device is a mobile device, such as a mobile telephone or tablet running a software application. In one embodiment, the external device receives data from the communication module 160 and after receiving the data, transmits the data to another location, such as a server computer.

In an illustrative embodiment according to the present invention, the communication module 160 is a BLE113 radio (Bluegiga Technologies, Duluth, Ga.). The BLE 213 radio transfers data through Bluetooth® connectivity. In one embodiment, the communication module 160 communicates data through Bluetooth® to a mobile device running a software application. In another embodiment, the communication module 160 communicates data through Bluetooth® to a home health monitor with cloud connectivity. In one embodiment, the device data is transmitted to an external device of a user, and the user determines if they would like to forward the information to payers, pharmacists, physicians, nurses, or other third parties. In one embodiment, the external device is a mobile device running a software application, and the software application allows a user to choose to whom the user would like to transmit data. In an alternative embodiment, the device data is transmitted directly to payers, pharmacists, physicians, nurses, or other third parties.

In an illustrative embodiment according to the present invention, the memory 140 can be configured to store one or more of force measurements, force data, motion measurements, and motion data. The processor 150 can be configured to retrieve data from the memory 140 for display to a user on the display 180 or for transmission to an external device via the communication module 160.

The timer 145 can be configured to communicate with the processor 150. The timer 145 can allow for time measurements to be correlated with measurements of one or more of the force sensors 130A,B and location sensors 170.

In some embodiments, the processor 150 can transmit one or more of force measurements, force data, motion measurements, and motion data to the display 180 for display to a user. In some embodiments, the diagnostic measurement device 100 may include a user interface configured to be presented on the display 180. The user interface may allow the user to initiate sensing by one or more of the force sensors 130A,B and motion sensors 170. In some embodiments, a user can initiate sensing by one or more of the force sensors 130A,B and motion sensors 170 by making a selection using the external device 185. In some embodiments, data relevant to patient health, such as diet information can be entered into the user interface and/or an external device 185.

In an illustrative embodiment a software application running on the diagnostic measurement device 100 or external device 185 can provide instructions to a user to perform certain actions for measurement by the force sensors 130A, B. For example, the software application can be configured to instruct a user to grip and/or squeeze the diagnostic measurement device 100 at the overmolds 110A and 110B. The diagnostic measurement device 100 can then measure grip strength based on data collected by the force sensors 130A,B. Similarly, the software application may direct a user to open and close their hand rapidly around the overmolds 110A and 110B. The force sensors can then detect when a force is applied and when the force is not applied in order to detect a time it takes to open and close the hand. The software application may also direct the user to touch one or more fingers to one or more particular locations, a location associated with one of the sensing surfaces for example, to detect data for measurement motor skills of the fingers or amount of force that can be applied by the fingers. The time taken to touch the particular locations may also be measured. In some instances, the software application may direct the user to touch a particular location repeatedly. The software application may also be configured to instruct the user to bend, rotate, or otherwise move the wrist, hand, and/or arm in one or more directions while holding the diagnostic measurement device 100. The motion sensors 170 can then collect data that can be used to determine a range of motion of the user's hand, wrist, and/or arm. The timer 145 can be used in conjunction with the motion sensors to measure the amount of time taken to complete particular bending, rotating, or moving tasks. Measurements produced based on data from one or more of the force sensors 130A,B and motion sensors 170 may be displayed on the display 180 or transmitted to one or more external device, such as external device 185, for display to one or more of users, payers, pharmacists, physicians, nurses, family members or any other desired parties. In some embodiments, measurements may be stored in the memory 140 of diagnostic measurement device or in a memory of an external device, such as external device 185. In some embodiments, previous measurements may be recalled by the memory 140 and displayed on the diagnostic measurement device 100 or external device 185 allowing for a comparison of measurements at different times throughout the progression of a disease. Measurements may be displayed as a chart, graph, or any other presentation format.

Instructions to the user may be displayed as text, images, and/or video to a user on the display 180 or on the external device 185. In some embodiments, the diagnostic measurement device 100 or external device 185 may provide an audible or haptic indication for to a user to perform a particular action for measurement by one or more of the force sensors 130A,B and motion sensors 170. For example, the diagnostic measurement device 100 can include a speaker to produce an audible indication. The diagnostic measurement device 100 may further include a haptic indicator to produce an indication that can be felt by a user, such as for example, a vibration. In one embodiment, the diagnostic measurement device 100 includes a small electric motor coupled to a weight in order to produce a vibration.

In some embodiments, the software application can initiate diagnostic testing by providing instructions to a user to perform particular actions based on a user input or selection using a user interface on the diagnostic measurement device 100 or on an external device, such as external device 185. The software application may also initiate diagnostic testing in response to an event such as an injection. In some embodiments, the diagnostic measurement device 100 may include one or more sensors configured to detect that an injection has occurred. In some embodiments, the software application may initiate diagnostic testing periodically at predetermined dates and/or times. In some embodiments, the software application may also be configured to provide reminders to the user that the software application will initiate diagnostic testing after a defined period of time. In some embodiments, the software application may prompt a user that a scheduled time to perform diagnostic testing has arrived and the user can decide whether to initiate instructions. In some embodiments, a third party, such as a physician, can transmit a signal to the device 100 or an external device, such as external device 185 to initiate diagnostic testing. In some embodiments, a third party, such as a physician, can communicate with the user through real time audio and/or video communication using the diagnostic measurement device 100 or an external device such as external device 185 to provide instructions for the user to perform certain actions for measurement by one or more of the load sensors 130A,B and/or location sensors 170.

In some embodiments, the diagnostic measurement device 100 or an external device running a software application, such as external device 185, can be configured to communicate with one or more external devices having sensors for conditions relevant to health and/or disease progression. For example the diagnostic measurement device 100 or an external 185 running a software application can be configured to communicate with and receive measurements from one or more of an activity tracking device, pedometer, sleep tracker, electronic scale, or medical devices. Such devices may measure or track activities or conditions such as exercise, sleep, weight, heart rate, and diet. Data from such devices may be transmitted to one or more of the diagnostic measurement device 100 or the external device running a software application for processing, display, storage in memory, and/or transmission to a third party. In some embodiments, one or more of the diagnostic measurement device 100 or external device 185 may include additional sensors for conditions relevant to health and/or disease progression. In some embodiments, the software application can be configured to provide instructions for a user to preform actions related to one or more of the sensors in the external devices having sensors for conditions relevant to health and/or disease progression and/or for the additional sensors of the diagnostic measurement device 100 and/or external device running a software application.

In an illustrative embodiment according to the present invention, one or more of the communication module 160, battery 120, processor 150, force sensors 130A,B, motion sensors 170, and memory 140, may be incorporated into a module designed to be fully integrated in the interior of an injection device. In an alternate embodiment, such a module may be designed to mount to the exterior of the injection device. For example, the module may be cylindrical in shape, and configured to reversibly mount to the exterior cover or cap of an autoinjector. In one embodiment, the module may include tabs, snaps, brackets or other means for mounting to the outside of an autoinjector.

Figure 5:
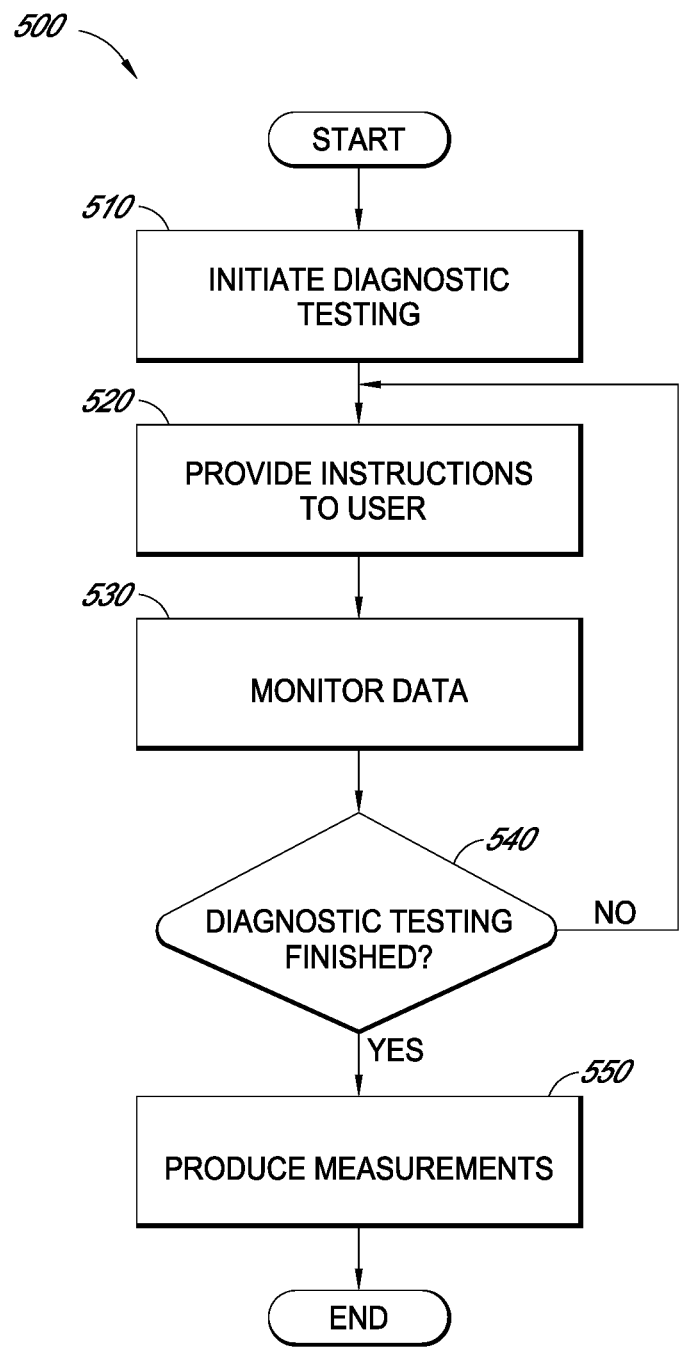
FIG. 5 depicts a flowchart of an embodiment of performing a diagnostic examination in accordance with an illustrative embodiment of the present invention.

FIG. 5 depicts a flowchart of a process 500 of an illustrative embodiment of a method for performing a diagnostic evaluation using a diagnostic measurement device such as diagnostic measurement device 100. The process 500 begins at a step 510, wherein diagnostic testing is initiated. The diagnostic testing may be initiated in response to a user input on the diagnostic measurement device or on an external device running a software application, at a predefined time or after a particular time interval, in response to an event such as an injection, or in response to receipt of a signal from an external device, for example, a device operated by a third party physician.

After initiation of diagnostic testing, the process 500 moves to a step 520, wherein an instruction is provided to the user. The instruction can be provided using visible, audible, or haptic indications. The instruction to the user may be displayed as text, images, and/or video to a user on a display, such as display 180, on the diagnostic measurement device or on an external device. The instruction directs a user to perform a particular action that can be measured for diagnostic assessment of health or disease progression. For example, an instruction may direct the user to grip and/or squeeze the diagnostic measurement device at locations associated with one or more force sensors, such as force sensors 130A,B, to open and close their hand rapidly around locations associated with one or more force sensors, or to touch one or more fingers to one or more locations associated with one or more force sensors. The instruction may also direct a user to bend, rotate, or otherwise move a wrist, hand, and/or arm in one or more directions while holding the diagnostic measurement device. A diagnostic measurement device may be configured for use with a plurality of different instructions. Each instruction can direct a user to perform an action that can be measured to provide data relevant to diagnostic assessment of health or disease progression. For example, gripping or squeezing actions can be measured to provide data relevant to the grip strength of the user. Bending, rotation, or movement of the wrist and/or hand can be measured to provide data relevant to the range of motion of a user.

After instructions are provided to the user, the process 500 moves to a step 530, wherein data is monitored by one or more sensors. The one or more sensors can include force sensors, such as sensors 130A,B, motion sensors, such as motion sensors 170, and/or a timer, such as timer 145. Data can be monitored by a particular sensor based on the particular action instructed in step 520 based on what type of measurements are relevant for that particular action. For example, force sensors may be used to monitor a gripping or squeezing action to provide data relevant to grip strength. Motion sensors can be used to monitor bending, rotation, or movement of the wrist, hand, and/or arm to provide data relevant to range of motion. A timer can be used in conjunction with one of the other sensors to determine an amount of time taken to perform a particular action or a duration of time between two actions.

After data is monitored by one or more sensors, the process 500 moves to a decision step 540, wherein a decision is made whether diagnostic testing is complete. If diagnostic testing is not complete, the process 500 returns to step 520 wherein another instruction can be provided to the user.

If diagnostic testing is complete, the process 500 moves to a step 550, wherein diagnostic measurements are produced. One or more measurements may be determined by a processor in the diagnostic measurement device, such as processor 150. In some embodiments, the sensor data and/or diagnostic measurements may be transmitted to an external device. In some embodiments, one or more measurements may be determined by an external device. The sensor data and/or diagnostic measurements may also be displayed on a display of the diagnostic measurement device or on an external device.

Implementations disclosed herein provide systems, methods and apparatus for a diagnostic measurement device. One skilled in the art will recognize that these embodiments may be implemented in hardware, software, firmware, or any combination thereof.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

In the foregoing description, specific details are given to provide a thorough understanding of the examples. However, it will be understood by one of ordinary skill in the art that the examples may be practiced without these specific details. For example, electrical components/devices may be shown in block diagrams in order not to obscure the examples in unnecessary detail. In other instances, such components, other structures and techniques may be shown in detail to further explain the examples.

Headings are included herein for reference and to aid in locating various sections. These headings are not intended to limit the scope of the concepts described with respect thereto. Such concepts may have applicability throughout the entire specification.

It is also noted that the examples may be described as a process, which is depicted as a flowchart, a flow diagram, a finite state diagram, a structure diagram, or a block diagram. Although a flowchart may describe the operations as a sequential process, many of the operations can be performed in parallel, or concurrently, and the process can be repeated. In addition, the order of the operations may be re-arranged. A process is terminated when its operations are completed. A process may correspond to a method, a function, a procedure, a subroutine, a subprogram, etc. When a process corresponds to a software function, its termination corresponds to a return of the function to the calling function or the main function.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A diagnostic measurement system for performing diagnostic measurement of a disease, comprising:
    an injection device configured to deliver medicament to a patient, the injection device comprising:
        a proximal end;
        a distal end;
        an upper portion positioned between the proximal end and the distal end;
        a lower portion positioned between the proximal end and the distal end, the lower portion being distal to the upper portion; and
        a plurality of force sensors disposed on lateral surfaces of the upper portion, each of the plurality of force sensors configured to mate with a finger of a plurality of fingers of the patient, wherein the plurality of force sensors are configured to measure a grip strength of the patient when the patient squeezes the injection device while the plurality of fingers of the patient are mated with the plurality of force sensors; and
    a processor configured to read data from the one or more force sensors and display a measurement related to the grip strength of the patient.

2. The system of claim 1, further comprising one or more motion sensors integrated with the injection device.

3. The system of claim 1, wherein the one or more force sensors are positioned within the interior of the injection device.

4. The system of claim 1, wherein the one or more force sensors are positioned on the exterior of the injection device.

5. The system of claim 1, further comprising a transmitter configured to transmit data to an external device.

6. The system of claim 1, further comprising a display for displaying the measurement.

7. The system of claim 1, wherein the processor is further configured to provide instructions to a user to perform one or more actions for detection by one or more of the force sensors.

8. The system of claim 7, further comprising one or more indicators, wherein the processor is configured to provide instructions by activating one or more indicators.

9. The system of claim 8, wherein the indicators comprise one or more of visible, audible, and haptic indicators.

10. The system of claim 7, wherein the processor is configured to provide instructions in response to one or more of receipt of a user input, receipt of a signal from an external device, a predefined time schedule, or an injection event.

11. The system of claim 1, wherein the grip strength is a measure of a compressive force of the patient's hand and fingers.

12. The system of claim 1, further comprising one or more overmolds positioned over the plurality of force sensors, the overmolds comprising one or more textured surfaces, each textured surface configured to provide an indication of a position for placement of one of the plurality of fingers of the patient for mating with one of the plurality of force sensors.

13. A diagnostic measurement system for performing diagnostic measurement of a disease, comprising:
- an injection device configured to deliver medicament to a patient;
- a plurality of force sensors disposed on lateral surfaces of the injection device and configured to measure a grip strength of the patient when the patient squeezes the lateral surfaces of the injection device;
- one or more overmolds positioned over the plurality of force sensors, the overmolds comprising one or more textured surfaces, each textured surface configured to provide an indication of a position for placement of a finger of a plurality of fingers of the patient for mating with one of the plurality of force sensors; and
- a processor configured to read data from the one or more force sensors and display a measurement related to the grip strength of the patient.

14. The system of claim 13, further comprising one or more motion sensors integrated with the injection device.

15. The system of claim 13, further comprising a transmitter configured to transmit data to an external device.

16. The system of claim 13, further comprising a display for displaying the measurement.

17. The system of claim 13, wherein the processor is further configured to provide instructions to a user to perform one or more actions for detection by one or more of the force sensors.

18. The system of claim 17, further comprising one or more indicators, wherein the processor is configured to provide instructions by activating one or more indicators.

19. The system of claim 18, wherein the indicators comprise one or more of visible, audible, and haptic indicators.

20. The system of claim 17, wherein the processor is configured to provide instructions in response to one or more of receipt of a user input, receipt of a signal from an external device, a predefined time schedule, or an injection event.

* * * * *